United States Patent [19]
Kersey et al.

[11] Patent Number: 6,024,087
[45] Date of Patent: Feb. 15, 2000

[54] EMERGENCY OXYGEN FLOWMETER ARRANGEMENT

[75] Inventors: Clifford G. Kersey, Oregon; Gordon G. Sansom; Frederick J. Montgomery, both of Sun Prairie, all of Wis.

[73] Assignee: Ohmeda Inc., Liberty Corner, N.J.

[21] Appl. No.: 08/948,114

[22] Filed: Oct. 9, 1997

[51] Int. Cl.$^7$ .................................................. A61M 15/00
[52] U.S. Cl. .............................. 128/203.12; 128/203.14; 128/203.25
[58] Field of Search ................... 128/203.12, 203.14, 128/203.25, 202.22

[56] References Cited

U.S. PATENT DOCUMENTS

| | | | |
|---|---|---|---|
| 4,442,856 | 4/1984 | Betz | 128/203.14 |
| 4,770,168 | 9/1988 | Rusz et al. | 128/203.14 |
| 5,335,652 | 8/1994 | Falb et al. | 128/203.14 |
| 5,531,218 | 7/1996 | Krebs | 128/202.22 |
| 5,546,931 | 8/1996 | Rusz | 128/203.14 |
| 5,732,693 | 3/1998 | Bathe et al. | 128/203.14 |
| 5,755,220 | 5/1998 | Ando | 128/203.25 |
| 5,806,513 | 9/1998 | Tham et al. | 128/203.14 |

FOREIGN PATENT DOCUMENTS

| | | | |
|---|---|---|---|
| 0361134A3 | 10/1990 | European Pat. Off. | |
| 2133714 | 8/1984 | United Kingdom | 128/203.25 |
| 2230843 | 10/1990 | United Kingdom | 128/203.25 |

*Primary Examiner*—Aaron J. Lewis
*Attorney, Agent, or Firm*—Andrus, Sceales, Starke & Sawall

[57] ABSTRACT

An emergency oxygen system that provides a flow of oxygen to the patient undergoing anesthesia in the event of a detected fault in the overall supply and mixing system of the anesthesia system. The normal design of such supply and mixing systems for an anesthesia system provides oxygen and at least one other gas that are mixed together in a desired proportion to be provided to a vaporizer and then to the anesthesia system as fresh gas. In the present system, a processor continuously monitors the output flows from those proportioning mixing valves. When the processor determines that those flows from the proportioning valves are off by a predetermined amount, indicative of a fault in the system, the processor immediately shuts off the supply of any gases other than oxygen and also provides a flow of oxygen to a bypass line that bypasses the oxygen proportioning valve, thus assuring a supply of oxygen to the patient despite the fault. A manual valve may be included in the bypass line so that the clinician can control the flow of oxygen and a flowmeter is provided so the clinician can visually note the flow and control that flow accordingly.

18 Claims, 2 Drawing Sheets

EMERGENCY OXYGEN FLOWMETER ARRANGEMENT

BACKGROUND

The present invention relates to anesthesia systems used to provide an anesthetic agent to a patient undergoing an operation.

In general, anesthesia systems are utilized in operating rooms and comprise various equipment necessary to anesthetize the patient and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient.

In one typical anesthesia system, the overall flow of gases to and from the patient may be in a generally closed circuit, commonly referred to as the circle system, that is, the patient is connected to a substantially closed volume supply of gases and rebreathes certain of those exhaled gases supplemented by fresh gas.

As the driving force to the circle breathing circuit, and, of course, to the patient, a ventilator is used and which basically breathes for the patient since the patient is under anesthesia and is unable to carry out the normal spontaneous breathing functions. The ventilator, therefore, provides a quantity of the gas containing a predetermined metered quantity of the anesthetic agent along with other gases such as nitrous oxide and, of course, a life sustaining percentage of oxygen.

That gas containing the anesthetic may typically be delivered through an intermediate mechanism such as a bellows. In such case, the driving gas from the ventilator does not contain the anesthetic agent but is used to simply power the bellows to collapse that bellows to deliver the aforementioned anesthetic containing gas from the bellows to the patient. Instead of drive gas, other driving means such as an electromechanical or mechanical means are also used.

In any of the aforedescribed systems, the anesthetic laden gas is delivered to the inspiratory limb of the circle patient breathing circuit and is introduced into the patient to provide anesthesia to that patient. That anesthetic gas to the inspiratory limb is provided by a source of gases, including fresh gas, oxygen and generally nitrous oxide, that is mixed to a predetermined mixture in a gas mixer and the mixed gases are then passed through an agent vaporizer where the anesthetic agent is introduced into those gases.

In the expiratory limb of the circle patient breathing circuit, as the patient exhales, the exhalation gases pass through the expiratory limb where they are recirculated back to the inspiratory limb where they are again inhaled by the patient. In this manner, the system is closed and which allows the optimum use of the rather expensive anesthetic agent. If the fresh gas added to the circuit exceeds the net of gases taken up by the patient or leaked from the circuit, the excess gases are popped off via a pop-off valve.

In the use of such anesthesia machines, it is important to have various safety features to ensure that the system is operating properly and, in the event there is some fault, that there is a prompt recognition of that fault and an immediate means to override the fault condition or faulty component to insure the safety of the patient.

One such fault can occur in the gas mixer, that is, the mixer that combines oxygen and other carrier gases such as nitrous oxide and air to provide the fresh gas that is added to the patient breathing circuit during the normal course of anesthesia. Potential faults in the mixing system include a loss of one or more of the added gases, a failure in the mixing system, failure of a flow sensor and the like. In general, such mixers are controlled by a central processing unit that senses the various critical flows and establishes the conditions to make those flows the same as inputted by the clinician or determined automatically by the machine.

In the case of such failure or fault in the mixing or supply system of the fresh gas to the patient breathing circuit, it is important that some alternate measure be provided to the clinician as well as sufficiently notifying the clinician of the occurrence of the fault condition. As an advantage, the alternate measure can provide some manual control to the clinician so that not only is the fault condition recognized, but the clinician can continue the application of oxygen manually to continue the particular operation until the patient can safely be taken off anesthesia. Obviously, in the mixing and supply portion of the anesthesia machine, it is paramount that the patient continue to receive the life supporting amount of oxygen until the fault has been corrected or the operation has been safely terminated and the patient taken off the faulty anesthesia machine.

SUMMARY OF THE INVENTION

The anesthesia system of the present invention includes a means of detecting when there is a fault in the supply of fresh gas to the patient breathing circuit, be that failure a loss of supply of one or more of the mixing gases, a failure of a flow sensor or other possible faults that would cause the inaccurate supplying of the fresh gas to the anesthesia machine.

In particular, the present system monitors various flow sensors that are provided and which are monitored by a central processing unit to ensure that the flows detected are the flows that are established for the system, as established by the clinician or established by some automatic machine function.

Upon determining that the readings from the flow sensors are not within the range that is critical to the operation of the anesthesia system, the present system provides an alert to the clinician that there is a fault condition and automatically terminates the supply of the gases, other than oxygen, to the mixer. At the same time, a bypass system is provided in the oxygen supply system so as to bypass the proportioning valve that is then providing the proportion of the oxygen desired. As a preferred embodiment, that bypass system also includes a manual valve so that the clinician can thereafter manually adjust and set the amount of oxygen flowing into the anesthesia machine as fresh gas and preferably includes a flow sensor that can be visually monitored by the clinician so that the proper flow of oxygen can be established and maintained until the operation can be safely terminated.

By use of the present system, the patient is assured that a life supporting amount of oxygen is being provided despite the particular fault and further that the clinician has control of the flow of oxygen to the anesthesia machine. The other gases and the other valves for those gases in the mixing system are effectively taken out of the system and are immediately terminated.

Other objects, features and advantages of the present invention will be more apparent from the detailed description of the preferred embodiments set forth below, taken in conjunction with the accompanying drawings.

DETAILED DESCRIPTION OF THE INVENTION

Figure 1:
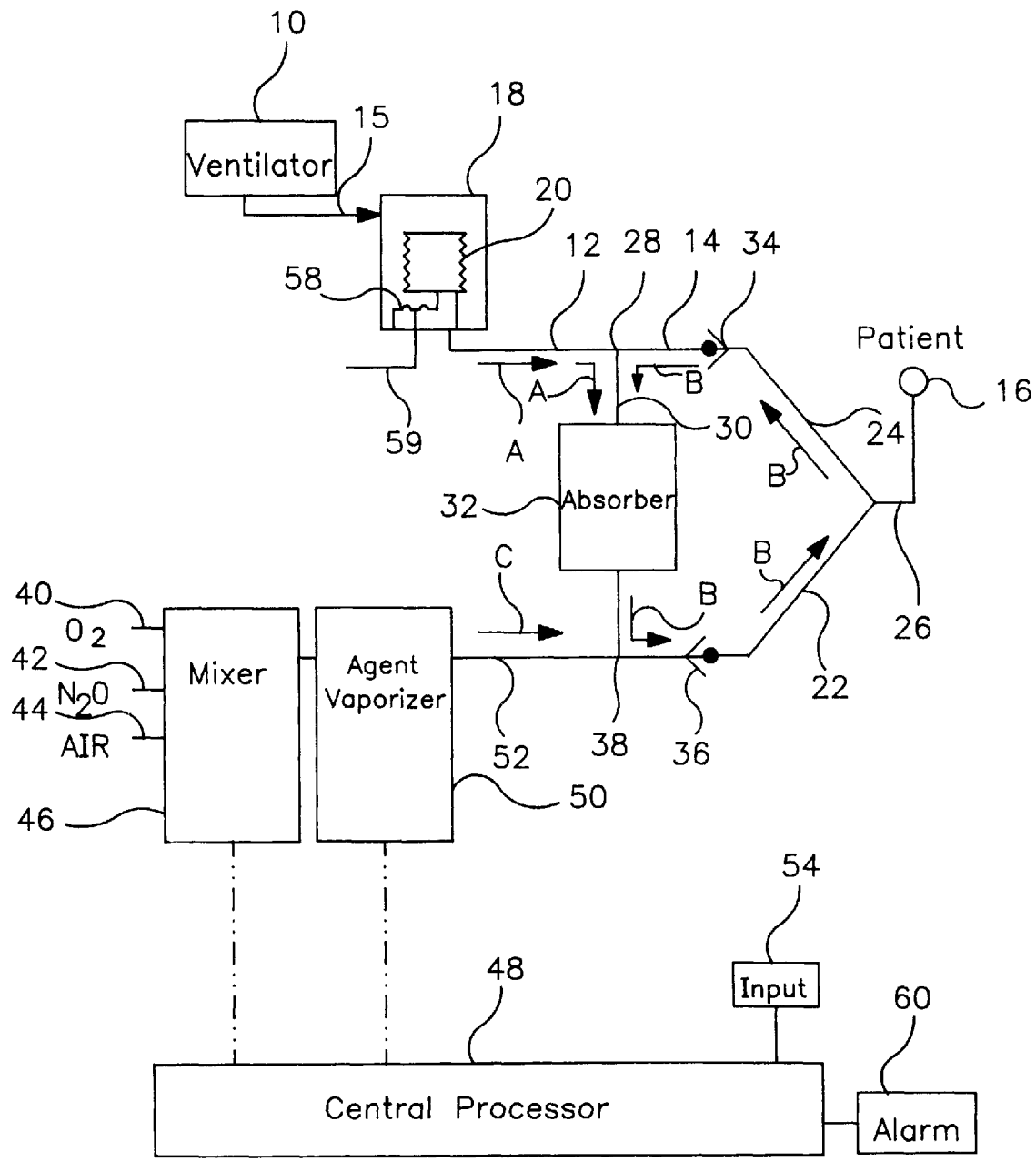
FIG. 1 is a block diagram of the components of an anesthesia system normally used in providing anesthesia to a patient.

Referring now to FIG. 1, there is shown a block diagram of a typical anesthesia system for providing anesthesia to a patient. As shown, a ventilator 10 is provided and which may be of the type shown and described in U.S. Pat. No. 5,315,989 assigned to the present applicant and the disclosure of which is incorporated herein by reference. The ventilator of the aforementioned U.S. Patent has an inhalation cycle and an exhalation cycle controlled by a central processing unit.

The ventilator 10 provides gas to the patient during the inhalation cycle via a conduit 12 to the patient breathing circuit 14 where it is delivered to the patient 16. The ventilator 10 typically includes a bellows container 18 and air or other powering gas is supplied to the bellows container 18 via conduit 15, exterior of the bellows 20 and which then collapses the bellows 20 to force gas within the bellows 20 to the patient 16.

As also noted in the aforementioned U.S. Pat. No. 5,315,989, the patient breathing circuit 14 itself conventionally includes an inspiratory limb 22 and an expiratory limb 24 and the patient 16 is connected to a wye connection 26 located intermediate the inspiratory and the expiratory limbs 22,24. The means of connection to the patient 16 may be an endotracheal tube, face mask or other interface between the patient 16 and the patient breathing circuit 14.

In conventional operation, gas is delivered to the patient 16 by means of a powering gas from ventilator 10 that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as sodalime.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the inspiratory limb 22 of the patient breathing circuit 14. That flow of fresh gas is provided from a source of gas, typically oxygen, air and nitrous oxide to aid in anesthetizing the patient. As shown in the Figure, there is a supply of oxygen 40, nitrous oxide 42 and air 44 and such supplies may be through a central piping system of a hospital or may be through the use of individual cylinders of such gases.

In any event, the gases are mixed in a gas mixer 46 in the proportion desired by the user. The actual control of the proportions and the flow through the gas mixer 46 is, in the preferred embodiment, controlled by a central processing unit (CPU) 48 as described in the aforementioned U.S. Patent. The mixed gas from the gas mixer 46 then passes through an agent vaporizer 50 where liquid anesthetic agent is vaporized and added to the stream of gas such that anesthetic laden gas continues into a conduit 52 and enters the patient breathing circuit 14 at the tee 38.

Again, in the preferred embodiment, the control of the agent vaporizer 50 is by means of the CPU 48 and which determines the percentage concentration of anesthetic agent that is in the gas that enters the patient breathing circuit 14 and thus that is supplied to the patient 16 to induce and maintain anesthesia.

The CPU 48 is, in turn, controlled by an input device 54 provided so that the clinician can input the data needed to determine the various parameters to provide the fresh gas flow and anesthetic concentration desired to anesthetize the patient. The input to the CPU 48 may be the flow of fresh gas to the patient as well as the concentrations of the various gases mixed in the gas mixer 46 and the concentration of anesthetic to be added to the mixed fresh gas by the agent vaporizer 50.

The overall flow scheme of the present conventional system is therefore such that the gas in the bellows 20 is forced by the ventilator 10 into conduit 12 in accordance with the arrows A during the inhalation cycle of the patient 16. The gas thus passes through the tee 28 and through absorber 32 where it further passes through tee 38 and into the inspiratory limb 22 of the patient breathing circuit 14. At tee 38, fresh gas containing a predetermined concentration of an anesthetic agent is joined with the gas from the bellows 20 and proceeds with the gases already circulating in patient breathing circuit 14 and administered to the patient 16.

When the patient exhales, the exhaled gas passes through the expiratory limb 24 of the patient breathing circuit 14 through tee 28 and continues through the conduit 12 and into the bellows 20. At the same time, fresh gas that continuously flows into the circuit 14 from conduit 52 is also directed towards the bellows 20 after passing through the patient breathing circuit 14. When the bellows 20 reaches the end of its travel, any excess gas is popped off from the bellows 20 via pop-off valve 58 and exits the system via conduit 59 and typically into a gas scavenging system, not shown.

During the inspiratory phase, the bellows 20 is driven downwardly by the ventilator 10. The unidirectional check valves 34 and 36 direct the gas from the bellows 20 to conduit 12 and through the absorber 32 where the gas is scrubbed of $CO_2$. Also directed is the fresh gas from conduit 52 towards the patient 16 via inspiratory limb 22 of breathing circuit 14.

As can be seen, therefore, the anesthesia system is basically a circle system where the gas continues to pass in a circle as shown by the arrows B with the addition of fresh gas and the anesthetic agent added to that gas in the direction of Arrow C as the gas passes around the circle.

Figure 2:
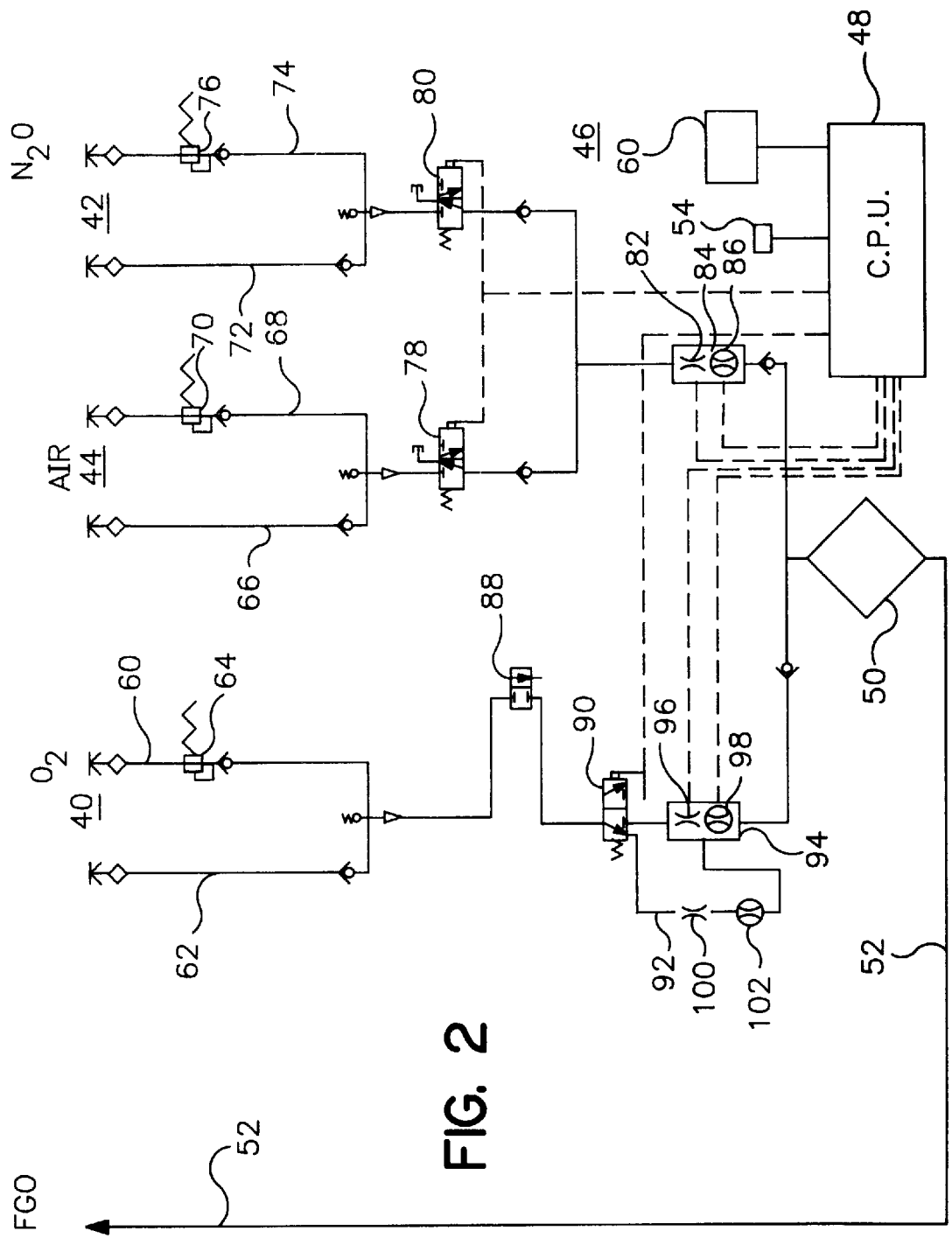
FIG. 2 is schematic view of the gas mixing system used with the anesthesia system of FIG. 1 and incorporating the emergency oxygen flowmeter system of the present invention.

Turning now to FIG. 2, there is shown a schematic view of the gas mixer 46 having the safety oxygen system constructed in accordance with the present invention.

As shown, there is an oxygen supply 40 and which may be by means of a cylinder supply entering conduit 60 or by means of the hospital piping system entering via the conduit 62. In the case of the former, regulator 64 is used to obtain the desired pressure to the system whereas with the pipeline, a regulator in the hospital system provides the desired pressure. Similarly, the supplies of air 44 and of nitrous oxide 42 are provided within conduits, respectively 66 and 68 for pipeline air and cylinder air with a regulator 70 in the latter and conduits 72 and 74 for pipeline nitrous and cylinder nitrous with an appropriate regulator 76 in the latter conduit.

Each of the supplies of air 44 and nitrous oxide 42 have solenoid activated on-off valves, respectively, as valves 78 and 80 to control the flow of air and nitrous oxide into the mixing system. Of course, only one of these gases can be activated at any particular time. The flow of the respective gases, air or nitrous oxide continue to a confluence and enter the module 82 in which is positioned an electronically controlled proportional valve 84 and a electronic flow sensor 86. The proportional valve 82 is controlled by the CPU 48 in accordance with the desired mixture of gases to be introduced to the vaporizer 50 and may be a set value by a clinician or may be determined by further automatic control by the anesthesia machine. The flow sensor 86 provides information to the CPU 48 indicative of the flow of the added gases (gases other than oxygen) to the vaporizer 50 and the CPU 48 verifies that the correct flow is detected at the flow sensor 86 and is in accord with the flow of gas that has been determined to be correct.

Taking the oxygen source 40, again the oxygen gas passes through an on-off valve 88 that controls the admission of oxygen to the system. A two position solenoid operated valve 90 is located in the oxygen line and can be switched between the position shown in FIG. 2 where the oxygen is diverted to bypass conduit 92. In the alternate position of the valve 90, the oxygen is supplied to the module 94 having a electronically controlled solenoid proportional valve 96 and a electronic flow sensor 98. Again, the function of module 94 is similar to that of the module 82, that is, the proportional valve 96 is controlled by the CPU 48 to arrive at the desired mixture of oxygen and other gases and the flow sensor 98 supplies the information to the CPU 48 that verifies that the flow is of the correct value to obtain the expected proportion of gases to the vaporizer 50.

In the other position of the valve 90 shown in FIG. 2, the flow of oxygen is diverted to the bypass conduit 92 and returns upstream of the flow sensor 98 where the oxygen continues through the flow sensor 92. A variable valve, such as a needle valve 100 is in the bypass conduit 92 and which is preferable manually operable by the clinician in operating the anesthesia machine. Further, a flow meter 102 is located in the bypass conduit 92 and, in the preferred embodiment, provide a visual indication to the clinician of the flow of oxygen flowing in the bypass conduit 92 so that the clinician can properly adjust the needle valve 100 to select the proper flow of oxygen to the flow sensor and to the vaporizer 50. As may be seen, although the variable valve 100 and a visually perceptible flowmeter 102 are preferred, the bypass could include a fixed orifice instead of a needle valve and a flow indicator.

In the operation of the emergency oxygen system of the present invention, the CPU 48 continually monitors the signals from the flow sensors 98 and 86 and thus can ensure that the flows of oxygen and other gases are set so as to provide the correct flows as determined by an input by the clinician or by some automatic control of the anesthesia machine itself.

Accordingly, when the CPU 48 notes that either of the flow sensors 98 or 86 is delivering a flow that is not within a predetermined window, for example, plus or minus ten percent of the expected value of flows, the CPU 48 determines that a fault condition exists. As indicated, that fault may be a failure in the supply of a gas, a failure of a sensor, proportional valve or the like.

In any event, the CPU 48 recognizes that there is a fault in the system and take the appropriate action. The CPU 48 immediately moves the valves 78 and 80 to the closed position to shut off the supply of nitrous and air to the mixing system. At the same time, the CPU 48 also moves the valve 90 to the position shown in FIG. 2 and thus diverts the supply of oxygen to the bypass conduit where the clinician can take control and utilize the manual needle valve 100 and the visual flowmeter 102 to control he oxygen to the vaporizer 50.

As a further feature of the present system, the system may be manually operated by the clinician activating a switch, such as a push-button 54 to cause the CPU 48 to immediately activate the bypass valve 90 to by pass the proportioning valve 96 and to shut off the valves 78 and 80 to stop the flow of air and nitrous oxide to the system.

Thus, the emergency oxygen system assures a flow of oxygen to the vaporizer 50 and the patient can continue to receive a life supporting supply of oxygen even though one or more of the components of the gas mixer has failed. As an additional feature, the existence of the fault condition causes an alarm 60 so that the clinician can recognize that the fault condition exists and that the appropriate action need be taken to control the flow of oxygen through the bypass conduit 92.

We claim:

1. An emergency oxygen system for an anesthesia system, said system comprising;

an oxygen conduit for delivering oxygen from a source of oxygen to an outlet, a gas conduit for delivering at least one other gas from a source of at least one other gas, said gas conduit having a shut-off valve in said conduit for controlling the flow of gas from said source of said at least one other gas, a first flow control valve in said oxygen conduit and a second flow control valve in said gas conduit, said first and second flow control valves adapted to establish a desired proportion of oxygen and said at least one other gas to supply a mixed gas in the desired proportion to said outlet through a supply conduit coupled to said oxygen conduit and gas conduit, a processor controlling the condition of said first and second flow control valves to achieve the desired proportion of oxygen and said at least one other gas at said outlet, gas sensors located downstream of each of said first and second flow control valves and upstream of said supply conduit, to monitor the mixture of gases from said first and second flow control valves to determine that said control valves are providing the desired proportion of oxygen and the at least one other gas, a bypass conduit for said oxygen conduit and connected so as to allow oxygen to bypass said first flow control valve, said bypass conduit having a means to control the flow of gas through said bypass conduit, means to close the shut off valve in the said gas conduit if the said gas sensors indicate the proportion of oxygen is not within a desired range, and alarm means to provide an indication to a user that the proportion of oxygen is not within the desired range.

2. An emergency oxygen system for an anesthesia system as defined in claim 1 wherein said means to control the flow of gas in said bypass conduit is a needle valve.

3. An emergency oxygen system for an anesthesia system as defined in claim 1 wherein said means to close the shut off valve further prevents oxygen from flowing through said first flow control valve.

4. An emergency oxygen system for an anesthesia system as defined in claim 1 wherein said first flow control valve and said second flow control valves are both proportioning valves.

5. An emergency oxygen system for an anaesthesia system as defined in claim 1 wherein said bypass conduit is further defined as connected to allow oxygen to bypass said first and second control valves.

6. An emergency oxygen system for an anesthesia system, said system comprising;
   an oxygen conduit for delivering oxygen from a source of oxygen to an outlet,
   a gas conduit for delivering at least one other gas from a source of at least one other gas, said gas conduit having a shut-off valve in said conduit for controlling the flow of gas from said source of said at least one other gas,
   a first flow control valve in said oxygen conduit and a second flow control valve in said gas conduit, said first and second flow control valves adapted to establish a desired proportion of oxygen and said at least one other gas to supply the mixed gas in the desired proportion to said outlet,
   a processor controlling the condition of said first and second flow control valves to achieve the desired proportion of oxygen and said at least one other gas at said outlet,
   gas sensors located downstream of said first and second flow control valves to monitor the mixture of gases from said first and second flow control valves to determine that said control valves are providing the desired proportion of oxygen and the at least one other gas,
   a bypass conduit for said oxygen conduit and connected so as to allow oxygen to bypass the first flow control valve in said oxygen conduit and the second flow control valve in said gas conduit, a bypass valve having a first condition where the oxygen passes through said first flow control valve and a second condition wherein said oxygen flows through said bypass conduit around said first and second flow control valves, said bypass conduit having a means to control the flow of oxygen in said bypass conduit and further having a means to monitor the flow in said bypass conduit, and
   alarm means responsive to a gas sensor to provide an indication to a user when the concentration of oxygen is not the desired proportion whereby said bypass valve can be activated to divert said flow of oxygen to said bypass conduit.

7. An emergency oxygen system for an anesthesia system as defined in claim 6 wherein said bypass valve is manually operable by a user.

8. An emergency oxygen system for an anesthesia system as defined in claim 6 wherein said bypass valve is electrically operated by a signal from said processor.

9. An emergency oxygen system for an anesthesia system as defined in claim 6 wherein said flow control valves are proportioning valves.

10. An emergency oxygen system for an anesthesia system as defined in claim 6 wherein said at least one other gas comprises air supplied through an air conduit and nitrous oxide supplied through an nitrous oxide conduit.

11. An emergency oxygen system for an anesthesia system as defined in claim 10 wherein said nitrous conduit and said air conduit each include separate shut-off valves.

12. An emergency oxygen system for an anesthesia system as defined in claim 6 wherein said oxygen flow sensor in said bypass line comprises a flow tube visually readable by the user.

13. An emergency oxygen system for an anesthesia system, said system comprising:
    an oxygen conduit adapted to be connected to a source of oxygen for delivering the oxygen to an outlet,
    a gas conduit adapted to be connected to a source of a gas for delivering the gas to an outlet, said gas conduit having a shut-off valve for controlling the flow of gas from the source through said gas conduit,
    a first flow control valve in said oxygen conduit and a second flow control valve in said gas conduit, said flow control valves adapted to establish a desired proportion of oxygen and gas to supply a mixture of oxygen and gas in a desired proportion to said outlet,
    a processor controlling the condition of said first and second flow control valves to achieve the desired proportion of oxygen and gas to said outlet,
    an oxygen flow sensor in said oxygen conduit and a gas flow sensor in said gas conduit, said processor adapted to monitor the flow sensors to determine that said first and second flow control valves are providing the desired flows of oxygen and gas, and
    a bypass conduit for said oxygen conduit and connected so as to allow oxygen to bypass the first flow control valve, a bypass valve having a first condition wherein the oxygen passes through said first flow control valve and a second condition wherein said oxygen flows through said bypass conduit around said first flow control valve,
    said processor adapted to determine when the flows sensed by said oxygen flow sensor and said gas flow sensor are not within a predetermined range of flows thereupon closing said shut off valve and operating said bypass valve to said second condition to divert oxygen around said first flow control valve to said outlet.

14. An emergency oxygen system for an anesthesia system as defined in claim 13 wherein said bypass conduit includes a means to control the flow of oxygen in said bypass conduit and further has a means to monitor the flow in said bypass conduit.

15. An emergency oxygen system for an anesthesia system as defined in claim 13 wherein said means to control the flow of oxygen comprises a manually operable needle valve.

16. An emergency oxygen system for an anesthesia system as defined in claim 14 wherein said means to monitor the flow in said bypass conduit comprises a flow meter visually perceptible by the user.

17. An emergency oxygen system for an anesthesia system, said system comprising;
    an oxygen conduit for delivering oxygen from a source of oxygen to an outlet,
    a gas conduit for delivering at least one other gas from a source of at least one other gas, said gas conduit having a shut-off valve in said conduit for controlling the flow of gas from said source of said at least one other gas,
    a first proportioning valve in said oxygen conduit and a second proportioning valve in said gas conduit, said proportioning valves adapted to establish a desired proportion of oxygen and said at least one other gas to supply the mixed gas in the desired proportion to said outlet, a processor controlling the condition of the proportioning valves to achieve the desired proportion of oxygen and said at least one other gas at said outlet, an oxygen flow sensor in said oxygen conduit and a gas flow sensor in said gas conduit downstream, respectively, of said first and second proportioning valves, said processor adapted to monitor the flow sensors to determine that the proportioning valves are providing the desired flows of oxygen and the at least one other gas, a bypass conduit for said oxygen conduit and connected so as to allow oxygen to bypass the proportioning valve in said oxygen conduit, a bypass valve having a first condition where the oxygen passes through said first proportioning valve and a second condition wherein said oxygen flows through said bypass conduit around said first proportioning valve, said bypass conduit having a means to control the flow of oxygen in said bypass conduit and further having a means to monitor the flow in said bypass conduit, said processor adapted to determine when the flows sensed by said oxygen flow sensor and said gas flow sensor are not within a predetermined range of flows necessary to produce the desired proportion of oxygen and said at least one other gas, said processor thereupon closing said shut off valve and operating said bypass valve to said second condition to divert oxygen around said first proportioning valve to said outlet.

18. An emergency oxygen system for an anesthesia system, said system comprising;

an oxygen conduit adapted to be connected to a source of oxygen for delivering the oxygen to an outlet, a gas conduit adapted to be connected to a source of a gas for delivering the gas to an outlet, said gas conduit having a shut-off valve for controlling the flow of gas from the source through said gas conduit, a first flow control valve in said oxygen conduit and a second flow control valve in said gas conduit, said flow control valves adapted to establish a desired proportion of oxygen and gas supply a mixture of oxygen and gas to in a desired proportion to said outlet, a processor controlling the position of said first and second flow control valves to achieve the desired proportion of oxygen and gas to said outlet, an oxygen flow sensor in said oxygen conduit and a gas flow sensor in said gas conduit to monitor the mixture of gases from said first and second control valves to determine that said control valves are providing the desired proportion of oxygen and gas, a bypass conduit for said oxygen conduit and connected so as to allow oxygen to bypass the first flow control valve, said bypass conduit having a means to control the flow of gas through said bypass conduit, means to close the shut off valve in said gas conduit when said oxygen and gas flow sensor indicates that the proportion of oxygen is not within the desired proportion, and alarm means to alert a user that the proportion of oxygen is not of the desired proportion in the mixture of oxygen and gas.

* * * * *